US00PP37234P2

(12) United States Plant Patent
Andres Jimenez

(10) Patent No.: US PP37,234 P2
(45) Date of Patent: Jan. 27, 2026

(54) ***ARISTERIA* PLANT NAMED 'D BLUE MOON'**

(50) Latin Name: *Aristeria beguinii*
Varietal Denomination: D BLUE MOON

(71) Applicant: Deltacactus S.L., Amposta (ES)

(72) Inventor: Javier Andres Jimenez, La Rapita (ES)

(73) Assignee: DeltaCactus S.L. (ES)

( * ) Notice: Subject to any disclaimer, the term of this patent is extended or adjusted under 35 U.S.C. 154(b) by 0 days.

(21) Appl. No.: 19/194,472

(22) Filed: Apr. 30, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan Mccormick Ewoldt
*Assistant Examiner* — Zachariah Allan Kay

(57) ABSTRACT

A new and distinct cultivar of *Aristeria* plant named 'D Blue Moon' is disclosed, characterized by tight and uniform rosette shape. Foliage is uniquely colored Green NN137A. The new variety is an *Aristeria*, typically produced as an ornamental plant.

2 Drawing Sheets

Figure 1:
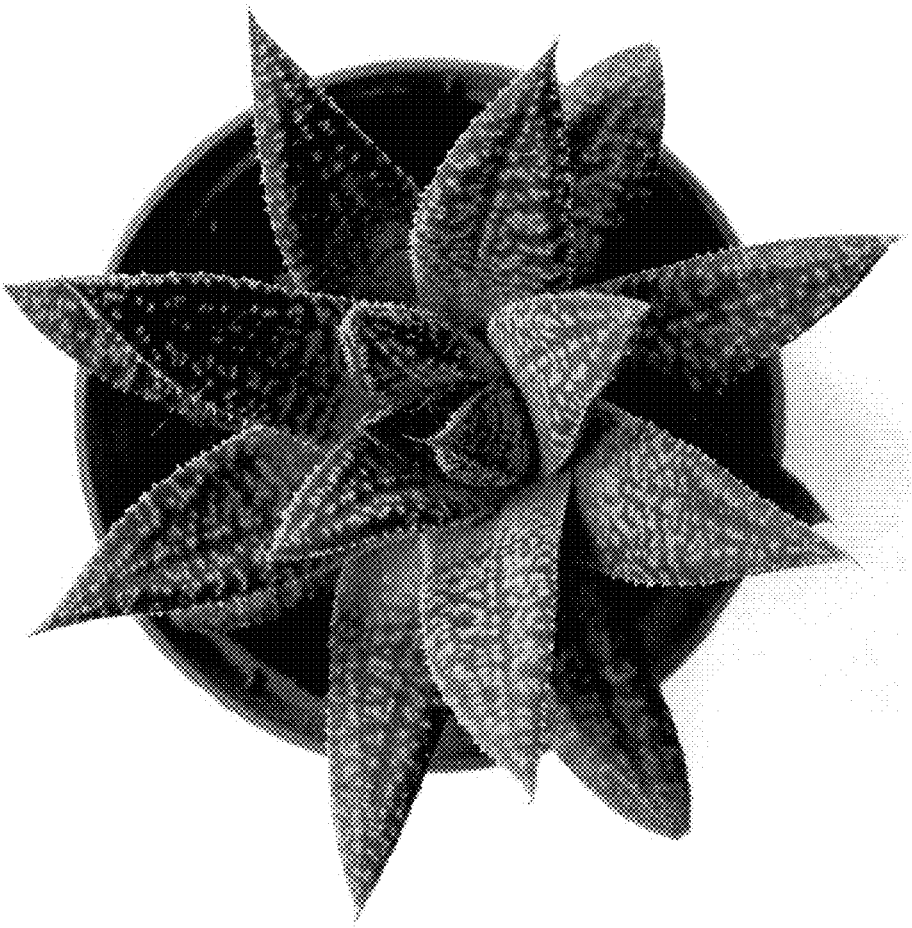

Latin name of the genus and species: *Aristeria beguinii.*
Variety denomination: 'D BLUE MOON'.

BACKGROUND OF THE INVENTION

The new cultivar is a product of a planned breeding program by the inventor, to produce distinct and better performing varieties. The seed parent is the inventor's own hybrid *Gasteria carinata* #1018, unpatented. The pollen parent is the inventor's own hybrid, *Aristaloe aristata* #2001, unpatented. The crossing resulting in the new cultivar was made in 2019 at a nursery in Amposta, Spain. 'D BLUE MOON' was found and selected by the inventor in March 2021 at the same location in Amposta, Spain.

Asexual reproduction of the new cultivar 'D BLUE MOON' was first performed in Amposta, Spain in March 2021, by vegetative cuttings. 'D BLUE MOON' has since produced several generations and has shown that the unique features of this cultivar are stable and reproduced true to type.

SUMMARY OF THE INVENTION

The cultivar 'D BLUE MOON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'D BLUE MOON.' These characteristics in combination distinguish 'D BLUE MOON' as a new and distinct *Aristeria* cultivar:

1. NN137A foliage color.
2. Tight and uniform rosette shape.

PARENTAL COMPARISONS

Plants of the new cultivar 'D BLUE MOON' are similar to the seed parent in most horticultural characteristics. However, plants of the new variety differ in the following:

1. Plants of the new variety are rosette-like, having a radial symmetry, while plants of the seed parent are not rosette-shaped, but have single axis symmetry.

Plants of the new cultivar 'D BLUE MOON' are similar to the pollen parent in most horticultural characteristics. However, plants of the new variety differ in the following:

1. Leaf color of the new variety is green (NN137A and 138B), while the leaf color of the pollen parent is deep green (Green 139A).
2. Leaves of the new variety are much thicker than leaves of the pollen parent.

COMMERCIAL COMPARISONS

'D BLUE MOON' can be compared to the commercial variety *Gasteraloe* 'D Delta', U.S. Plant Pat. No. 30,905. The two varieties are similar in most horticultural characteristics; however, the new variety differs in the following:

1. Leaf color of the new variety is green (NN137A and 138B), while the leaf color of this comparator is deep green (147A and 139A).
2. Leaves of the new variety are thicker and more upright than leaves of this comparator.

'D BLUE MOON' can be compared to the unpatented commercial variety *Gasteraloe* 'WT01', U.S. Plant Pat. No. 22,012. The two varieties are similar in most horticultural characteristics; however, the new variety differs in the following:

1. Leaf color of the new variety is green (NN137A and 138B), while the leaf color of this comparator is lighter green (N137A and Green-White 157B).
2. Leaves of the new variety are thicker and more upright than leaves of this comparator.
3. Pustules, called "dots" in U.S. Plant Pat. No. 22,012 are colored Greyed-Green 191B and 191C on foliage of 'C Blue Moon'. These structures are colored White N155C in 'WT01'.

BRIEF DESCRIPTION OF THE PHOTOGRAPHS

The accompanying photograph in FIG. 1 illustrates in full color a typical plant of 'D BLUE MOON' grown in a greenhouse in Amposta, Spain. This plant is approximately 50 weeks old, shown in a 9 cm container.

Figure 2:
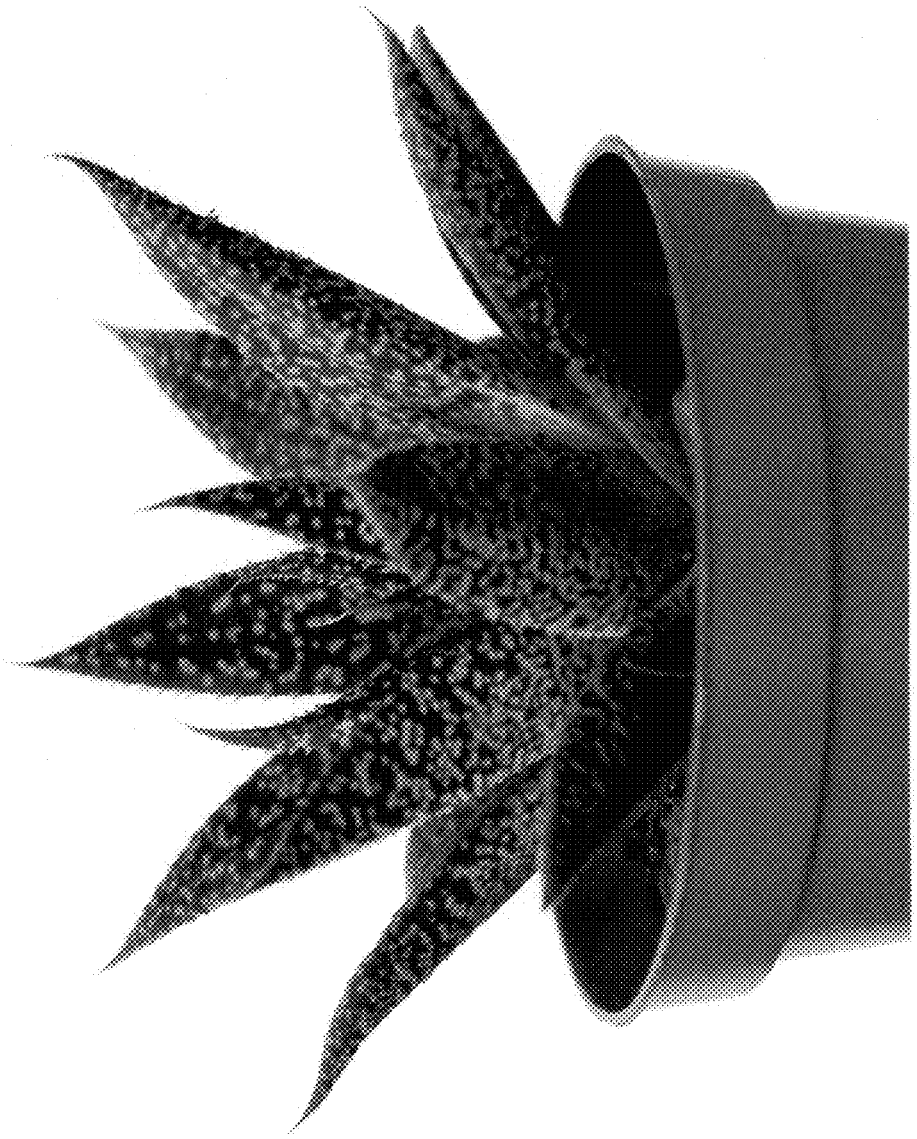

FIG. 2 illustrates a side-view of the same plant. The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Color Chart, 2015 edition, except where general terms of ordinary dictionary significance are used. The following observations and measurements describe 'D BLUE MOON' plants in a glass greenhouse in Amposta, Spain. Temperatures ranged from 18° C. to 20° C. during the day, and 15° C. to 18° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aristeria beguinii* 'D BLUE MOON'.

Age of the Plant Described: 50 weeks.

PROPAGATION

Time to initiate roots: 20 days in summer; 20 days in winter at 20° C.

Time to produce rooted cutting: 80 days in summer; 90 days in winter at 20° C.

Root Description: Fibrous, thick, moderately dense and freely-branching. White in color with yellow tips, not accurately measured with the RHS chart.

Propagation Method: Vegetative cuttings.

PLANT

Plant Type: Perennial potted plant.

Plant Shape: Flattened globular.

Growth Habit: Basal rosette.

Container size: 6 cm pots and larger.

Height: Average 8.4 cm; no flowering observed.

Plant Spread: Average 11.5 cm.

Branching Characteristics: Leaves in basal rosettes; 1 basal rosette per plant.

FOLIAGE

Leaf:

*Arrangement*.—Single rosette.

*Quantity*.—Average 20 leaves per rosette.

*Average Length*.—6.9 cm.

*Average Width*.—2 cm.

*Thickness*.—0.7 cm.

*Shape of blade*.—Broad lanceolate to near oblong, succulent.

*Whole leaf aspect*.—Very sightly concave.

*Apex*.—Narrow apiculate with a soft mucronate tip.

*Base*.—Broad cuneate.

*Margin*.—Finely serrate-dentate, average length and height of teeth: 0.5 mm, colored RHS Greyed-Green 190D.

*Texture of top surface*.—Moderately pustulate, placed irregularly on lamina, average width: 0.1 cm, average height: 0.3 mm and less, colored RHS Greyed-Green 191B.

*Texture of bottom surface*.—Densely pustulate, placed irregularly on lamina, average width: 0.1 cm, average height: 0.3 mm and less, colored 24 RHS Greyed-Green 191C.

*Pubescence*.—None.

*Rugosity*.—Both sides non-rugose.

*Luster: Upper side: Matte. Under side: Matte.*

*Color*.—Young foliage upper side: RHS Green NN137A lightly flushed Yellow-Green 147A; fading to Yellow-Green N145B towards base. Young foliage under side: RHS Green NN137A; fading to Yellow-Green N148D towards base. Mature foliage upper side: A RHS Green NN137A lightly flushed Yellow-Green 147A; fading to Green 138B towards base; base White N155C and 156C. Mature foliage under side: A blend of RHS Green NN137A to Yellow-Green 147A; fading to Yellow-Green 143A and 143C towards base; base White N155C.

*Venation*.—Pattern: Parallel. Color, upper side: Indistinguishable from leaf blade. Color, under side: Indistinguishable from leaf blade.

FLOWER

Flowering not observed to date.

REPRODUCTIVE ORGANS

Not observed to date.

OTHER CHARACTERISTICS

Seeds and fruits: Not observed to date.

Temperature tolerance: Unknown, at least tolerant to temperatures up to 40° C. USDA zone 10 to 12.

Tolerance to wind and rain: Low tolerance to rain; high tolerance to wind.

Disease/pest resistance: Similar to x*Aristeria* varieties. Typical insect pests include mealybugs (*Pseudococcidae* spp.), spider mites (*Tetranychidae* spp.) and scale insects (*Hemiptera* spp.). Typical diseases are fungal, *Anthracnose, Cercospora* or *Alternaria.*

What is claimed is:

1. A new and distinct cultivar of *Aristeria* plant named 'D Blue Moon' as herein illustrated and described.

* * * * *